United States Patent [19]
Kisalus

[11] Patent Number: 4,835,332
[45] Date of Patent: May 30, 1989

[54] USE OF TRIPHENYLPHOSPHINE AS AN ETHYLENE FURNACE ANTIFOULANT

[75] Inventor: John C. Kisalus, Houston, Tex.

[73] Assignee: Nalco Chemical Company, Naperville, Ill.

[21] Appl. No.: 238,784

[22] Filed: Aug. 31, 1988

[51] Int. Cl.$^4$ .......................... C07C 11/04; C10G 9/16
[52] U.S. Cl. ............................... 585/650; 208/48 HA; 208/48 K; 585/648; 585/950; 252/389.2; 252/389.4
[58] Field of Search ............. 208/48 AA; 252/389.24, 252/389.2; 44/640; 585/950, 650, 648

[56] References Cited

U.S. PATENT DOCUMENTS

| | | | |
|---|---|---|---|
| 3,531,394 | 9/1970 | Koszman | 208/48 |
| 3,647,677 | 3/1972 | Wolff et al. | 208/48 |
| 4,105,540 | 8/1978 | Weinland | 208/48 |
| 4,542,253 | 9/1985 | Kaplan et al. | 585/650 |
| 4,551,227 | 11/1985 | Porter et al. | 208/48 AA |
| 4,552,643 | 11/1985 | Porter et al. | 585/950 |
| 4,613,372 | 9/1986 | Porter et al. | 585/950 |

FOREIGN PATENT DOCUMENTS 935190 10/1973 Canada .......................... 208/48 AA

OTHER PUBLICATIONS

"Kinetics of Coke Deposition in the Thermal Cracking of Propane", K. M. Sundaram and G. F. Froment, *Chemical Engineering Science, 1979, vol. 34, pp. 635–644.*
"Coke Deposition in the Thermal Cracking of Ethane", K. M. Sundaram, P. S. VanDamme and G. F. Froment, *AIChe Journal,* Nov. 1981, vol. 27, No. 6, pp. 946–951.
"On-Line Gas Chromatographic Analysis of Hydrocarbon Effluents—Calibration Factors and Their Correlation", by J. L. Dierickx, P. M. Plehiers and G. F. Froment, *Journal of Chromatography,* 362(1986), pp. 155–174.

Primary Examiner—H. M. S. Sneed
Assistant Examiner—Helane Myers
Attorney, Agent, or Firm—John G. Premo; Anthony L. Cupoli; Donald G. Epple

[57] ABSTRACT

Triphenylphosphine prevents fouling in ethylene furnaces.

1 Claim, 3 Drawing Sheets

USE OF TRIPHENYLPHOSPHINE AS AN ETHYLENE FURNACE ANTIFOULANT

INTRODUCTION

Ethylene manufacture entails the use of pyrolysis or "cracking" furnaces to manufacture ethylene from various gaseous and liquid petroleum feed stocks. Typical gaseous feed stocks include ethane, propane, butane and mixtures thereof. Typical liquid feed stocks include naphthas, kerosene, gas oil and crude oil.

Fouling of the cracking furnace coils and transfer line exchangers (TLE's) occurs due to coking and polymer deposition. The fouling problem probably is the major operational difficulty experienced in running an ethylene plant. Depending on deposition rate, ehtylene furnaces must be periodically shut down for cleaning. In addition to periodic cleaning, "crash shut downs" are sometimes required due to dangerous increases in pressure or temperatures resulting from deposit build-up on furnace coils and TLE's. Cleaning operations are carried out either mechanically or by steam/air decoking.

Run lengths for ethylene furnaces average from one week to three months depending in part upon the rate of fouling of the furnace coils and TLE's. This fouling rate is in turn dependent upon the nature of the feed stock as well as upon furnace design and operating parameters. In general, however, heavier feed stocks and higher cracking severity result in an increased rate of furnace and TLE fouling.

In recent years, amine neutralized sulfonate treatments have been used in some ethylene plants to reduce furnace coil fouling. These compounds, however, have failed to prevent coking and fouling of TLEl's immediately down stream of the furnace. The failure in respect of the TLE's may be due to premature degradation of the treatments in the ethylene furnace which sees temperatures in the range 1,000°–1,700° F.

PRIOR ART

U.S. Pat No. 4,105,540 teaches that phosphate and phosphite mono and diesters in small amounts function as anti-foulant additives in ethylene cracking furnaces which are subjected to elevated temperature from about 500°–1,700° F.

U.S. Pat. No. 4,542,253 discloses that certain amine neutralization products of the compounds disclosed in U.S. Pat. No. 4,105,540 provide an improved ethylene cracking furnace anti-foulant.

The abstract of U.S. Pat. No. 4,551,227 describes the invention therein and reads as follows:

"The formation of carbon on metals exposed to hydrocarbons in a thermal cracking process is reduced by contacting such metals with an antifoulant selected from the group consisting of a combination of tin and phosphorus, a combination of phosphorus and antimony and a combination of tin, antimony and phosphorus."

U.S. Pat. No. 3,647,677 indicates that elemental phosphorus prevents coke formation in refining units.

U.S. Pat No. 3,531,394 shows certain phosphorus compounds as being anti-foulants in steam cracking processes.

As will be demonstrated hereafter, not all phosphorus-containing compounds provided equal protection to ethylene cracking furnaces in the prevention of coke formation therein.

THE INVENTION

The invention comprises a method for reducing fouling in ethylene cracking furnaces using petroleum feed stock which comprises treating the petroleum feed stock with an anti-fouling amount of triphenylphosphine.

A BRIEF DESCRIPTION OF THE DRAWINGS

Comparisons were made between the efficiency of triphenylphosphine and a commercial phosphorous-containing antifouling additive. The results are presented in the drawings of which:

THE DOSAGE

The dosasge involves treating the feed stock with at least 10 ppm and preferably 25–100 ppm of triphenylphosphine. In addition, it is preferred that plant equipment surfaces be pretreated with these compounds.

THE EVALUATION OF THE INVENTION

The test method involved the utilization of a laboratory reactor which duplicated the conditions found in an ethylene cracking furnace. For details see the publications "Kinetics of Coke Deposition in the Thermal Cracking of Propane", K. M. Sundaram and G. F. Froment, *Chemical Engineering Science,* 1979, Vol., 34 pp. 635–644; and "Coke Deposition in the Thermal Cracking of Ethane", K. M. Sundaram, P. S. VanDamme, and G. F. Froment, *AlChE Journal,* Nov., 1981, Vol. 27, No. 6., pg. 946.

EXAMPLES

Experimental conditions continuous addition of 200 ppm 5210 solution of some 20% active substance
a new pretreated, Inconel 600 cylinder
Hexane flow: 60 ml/hr
Water flow: 20 ml/hr
Ve/Fo*: 41 L.s/mol
dil water: 0.5 kg/kg

*Ve is equivalent reactor volume, 1. Fo is initial molar flow rate of hydrocarbons, mole/sec.
See publication entitled "Kinetics of Coke Deposition in the Thermal Cracking of Propane" by K. M. Sundaram and G. F. Froment, *Chemical Engineering Science,* 1979, Vol. 34, pp 635-644, published by Pergamon Press.

In the experiments, triphenylphoshine was compared against a commercial additive corresponding with the teachings of U.S. Pat. No. 4,542,253. This commercial additive containing 20% of active phosphorous copounds. The data was collected using an electro-balance. For more details of the technique, see the article, "Calibration Factors and Correlation", J. L. Dierickx, P. M. Plehiers, G. F. Froment—Journal of Chromatography, 362(1986), 155–174.

EXAMPLE I

Figure 1:
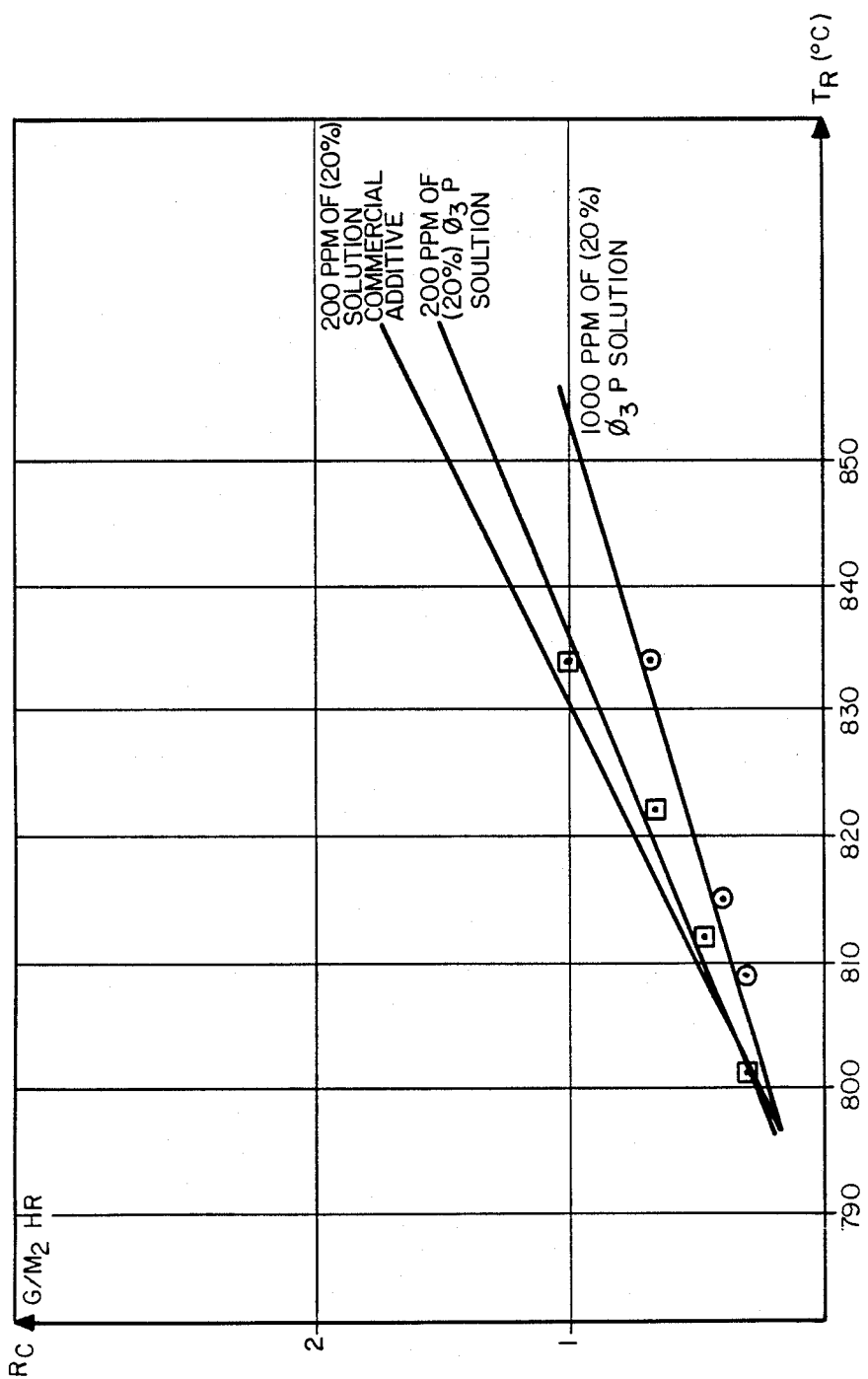
FIG. 1 shows asymptotic coking rates as a function of temperature.

Triphenylphosphine substantially reduces the coke formation in hexane cracking experiments. Its effect can be compared to that of the commercial additive assuming that the relationship between the commercial additive and blank runs are valid. They show almost coinciding rates of coke deposition at low temperatures (800° C.). However, a difference is noted as is shown in FIG. 1 for high temperatures. Some experiments with a higher concentration of additive are also carried out. A higher concentration of the addditive reduces the coke deposition much more. These results are also plotted in FIG. 1.

EXAMPLE 2

Figure 2:
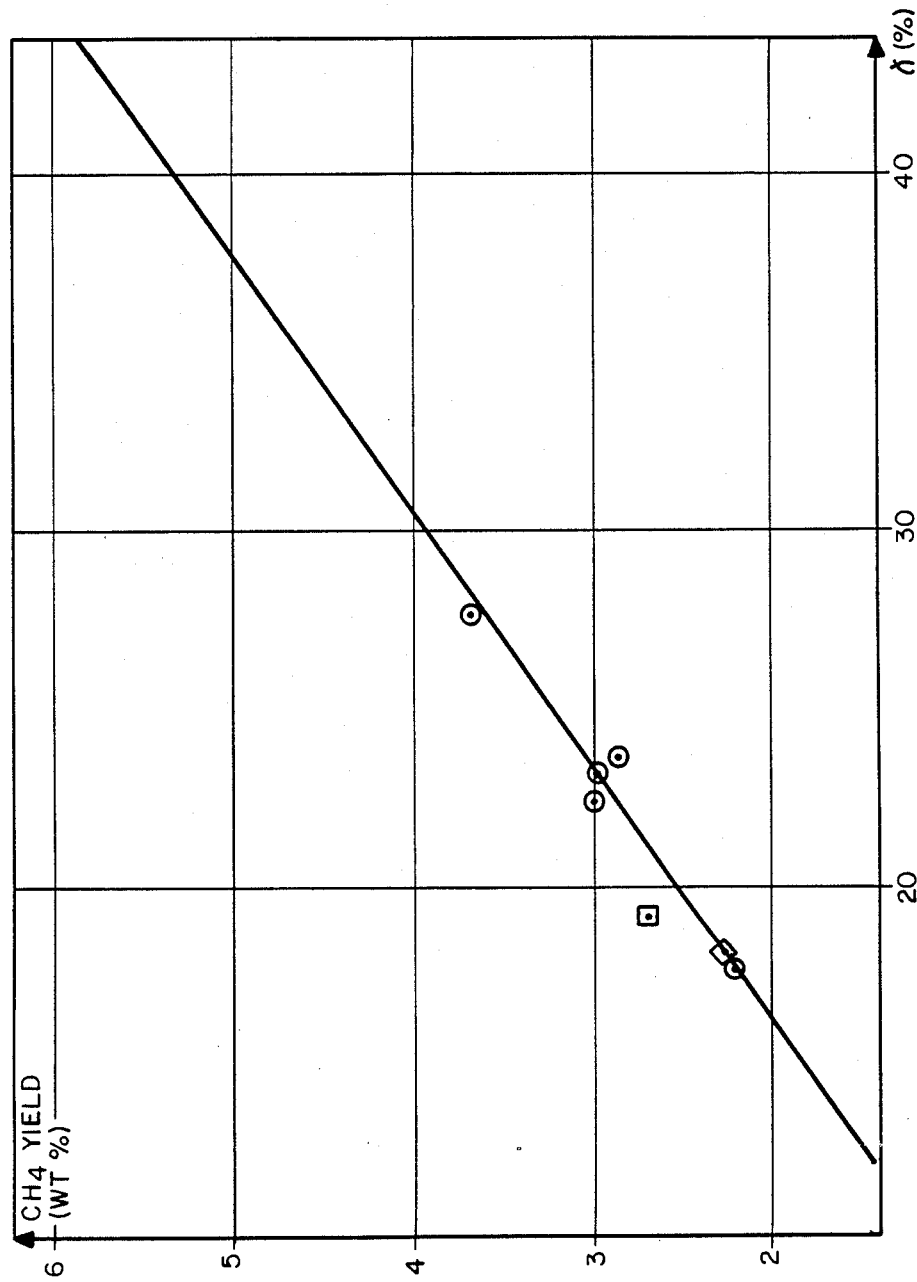
FIG. 2 shows conclation between $CH_4$ yield and conversion results of experiments with triphylphosphine vs. commercial additives.

In FIG. 2 the methane yields correlated to conversion for the experiments with triphenylphosphine are shown. This illustrates that the additive triphenylphosphine does not interact with the cracking mechanism to such a degree that shifts in the product distribution occur.

EXAMPLE 3

Figure 3:
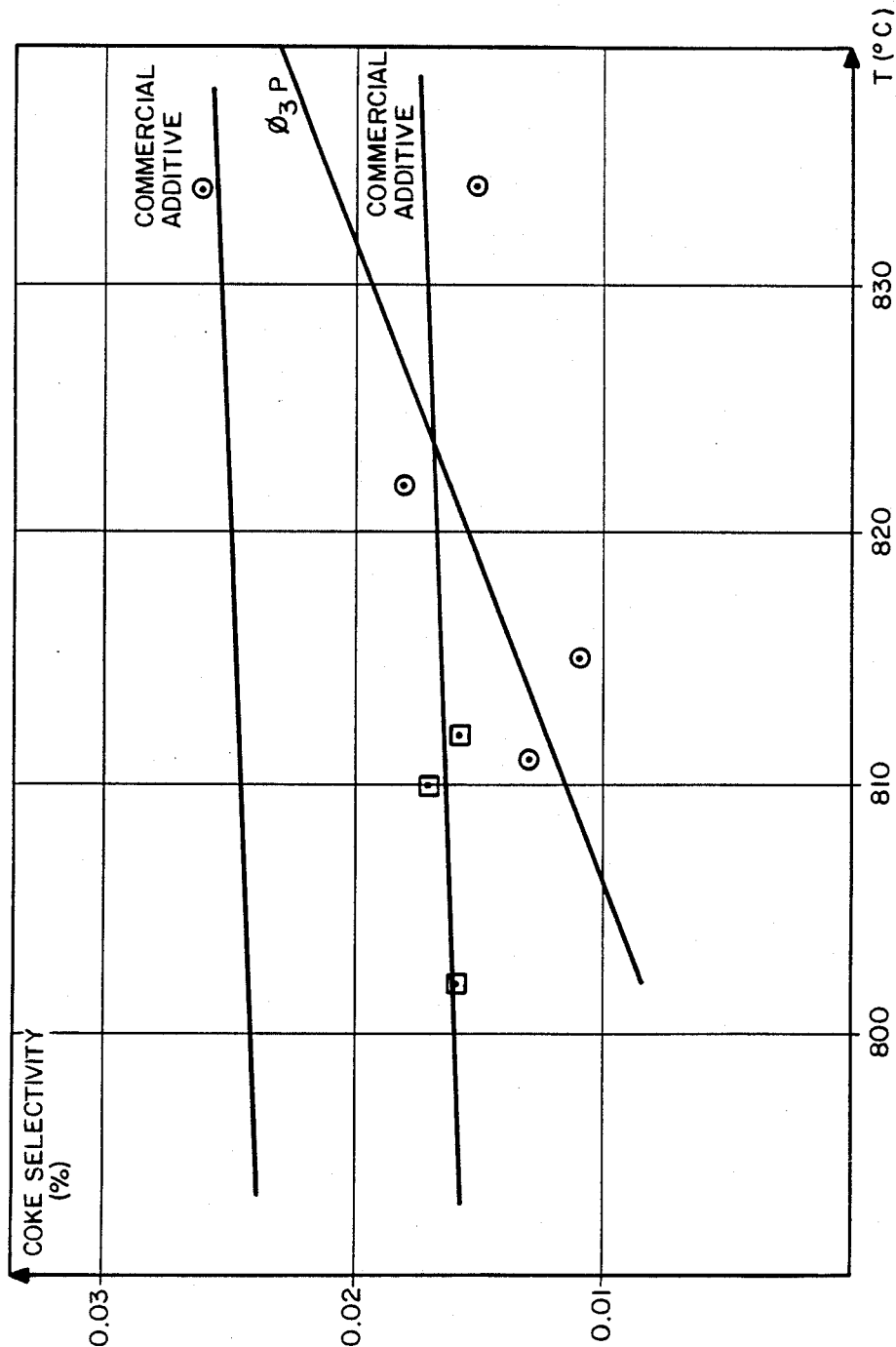
FIG. 3 shows selectivity vs. temperature.

Plotting coke selectivity versus temperature reveals a dependence on temperature for the additive triphenylphosphine. This was not observed with the commercial additive as shown in FIG. 3.

Having thus described my invention, it is described as follows. I claim:

1. A method for reducing fouling in ethylene cracking furnaces using petroleum feed stock which comprises feeding to the petroleum feed stock as the only antifouling additive an anti-fouling amount of triphenylphosphine.

* * * * *